United States Patent
Mansi et al.

(10) Patent No.: US 10,842,379 B2
(45) Date of Patent: Nov. 24, 2020

(54) MULTI-MODALITY IMAGE FUSION FOR 3D PRINTING OF ORGAN MORPHOLOGY AND PHYSIOLOGY

(71) Applicant: Siemens Healthcare GmbH, Erlangen (DE)

(72) Inventors: Tommaso Mansi, Plainsboro, NJ (US); Helene Houle, San Jose, CA (US); Sasa Grbic, Princeton, NJ (US); Andrzej Milkowski, Issaquah, WA (US)

(73) Assignee: Siemens Healthcare GmbH, Erlangen (DE)

(*) Notice: Subject to any disclaimer, the term of this patent is extended or adjusted under 35 U.S.C. 154(b) by 435 days.

(21) Appl. No.: 15/416,102

(22) Filed: Jan. 26, 2017

(65) Prior Publication Data

US 2017/0217102 A1 Aug. 3, 2017

Related U.S. Application Data

(60) Provisional application No. 62/288,481, filed on Jan. 29, 2016.

(51) Int. Cl.
*A61B 5/00* (2006.01)
*A61B 5/055* (2006.01)
(Continued)

(52) U.S. Cl.
CPC .......... *A61B 5/0035* (2013.01); *A61B 5/0044* (2013.01); *A61B 5/055* (2013.01);
(Continued)

(58) Field of Classification Search
CPC ....... A61B 5/055; A61B 6/032; A61B 8/5261; A61B 34/10; A61B 2034/105;
(Continued)

(56) References Cited

U.S. PATENT DOCUMENTS 7,916,919 B2  3/2011 Zheng et al.
8,577,177 B2  11/2013 Guetter et al.
(Continued)

OTHER PUBLICATIONS

Neumann et al., "Probabilistic Sparse Matching for Robust 3D/3D Fusion in Minimally Invasive Surgery", IEEE Transactions on Medical Imaging, 2015, vol. 34, No. 1, pp. 49-60.
(Continued)

*Primary Examiner* — Pinalben Patel

(57) ABSTRACT

A system and method for multi-modality fusion for 3D printing of a patient-specific organ model is disclosed. A plurality of medical images of a target organ of a patient from different medical imaging modalities are fused. A holistic mesh model of the target organ is generated by segmenting the target organ in the fused medical images from the different medical imaging modalities. One or more spatially varying physiological parameter is estimated from the fused medical images and the estimated one or more spatially varying physiological parameter is mapped to the holistic mesh model of the target organ. The holistic mesh model of the target organ is 3D printed including a representation of the estimated one or more spatially varying physiological parameter mapped to the holistic mesh model. The estimated one or more spatially varying physiological parameter can be represented in the 3D printed model using a spatially material property (e.g., stiffness), spatially varying material colors, and/or spatially varying material texture.

44 Claims, 9 Drawing Sheets

(51) Int. Cl.
- *A61B 8/08* (2006.01)
- *A61B 6/03* (2006.01)
- *A61B 34/10* (2016.01)
- *G06F 19/00* (2018.01)
- *G05B 19/4099* (2006.01)
- *B33Y 10/00* (2015.01)
- *B33Y 30/00* (2015.01)
- *B33Y 50/02* (2015.01)
- *B33Y 80/00* (2015.01)
- *B33Y 70/00* (2020.01)
- *B29C 64/386* (2017.01)
- *G16H 50/50* (2018.01)
- *B33Y 50/00* (2015.01)
- *G16H 40/63* (2018.01)
- *B29C 64/112* (2017.01)
- *B29C 64/20* (2017.01)
- *B29L 31/00* (2006.01)

(52) U.S. Cl.
CPC ............ *A61B 6/032* (2013.01); *A61B 8/485* (2013.01); *A61B 8/5261* (2013.01); *A61B 34/10* (2016.02); *B29C 64/112* (2017.08); *B29C 64/20* (2017.08); *B29C 64/386* (2017.08); *B33Y 10/00* (2014.12); *B33Y 30/00* (2014.12); *B33Y 50/00* (2014.12); *B33Y 50/02* (2014.12); *B33Y 70/00* (2014.12); *B33Y 80/00* (2014.12); *G05B 19/4099* (2013.01); *G06F 19/321* (2013.01); *G16H 40/63* (2018.01); *G16H 50/50* (2018.01); *A61B 2034/105* (2016.02); *A61B 2576/023* (2013.01); *B29L 2031/7532* (2013.01); *B29L 2031/7534* (2013.01); *G05B 2219/45172* (2013.01); *G05B 2219/49023* (2013.01)

(58) Field of Classification Search
CPC ............ A61B 5/0044; A61B 2576/023; A61B 5/0035; A61B 8/485; B29C 64/20; B29C 64/386; B29C 64/112; G06F 19/321; G05B 19/4099; G05B 2219/49023; G05B 2219/45172; B33Y 10/00; B33Y 30/00; B33Y 50/02; B33Y 80/00; B33Y 70/00; B33Y 50/00; B29L 2031/7532; B29L 2031/7534; G16H 40/63; G16H 50/50

See application file for complete search history.

(56) References Cited

U.S. PATENT DOCUMENTS

| | | | |
|---|---|---|---|
| 8,920,332 B2 | 12/2014 | Hong et al. | |
| 9,042,620 B2 | 5/2015 | Kohlberger et al. | |
| 9,129,053 B2 | 9/2015 | Mansi et al. | |
| 9,463,072 B2 | 10/2016 | Comaniciu et al. | |
| 10,149,618 B1* | 12/2018 | Tandon | A61B 5/0042 |
| 2010/0040272 A1 | 2/2010 | Zheng et al. | |
| 2012/0022843 A1 | 1/2012 | Ionasec et al. | |
| 2012/0078097 A1 | 3/2012 | Wang et al. | |
| 2013/0197881 A1 | 8/2013 | Mansi et al. | |
| 2014/0073907 A1* | 3/2014 | Kumar | A61B 10/00 600/414 |
| 2015/0025666 A1 | 1/2015 | Olivieri et al. | |
| 2015/0073765 A1 | 3/2015 | Boettger et al. | |
| 2015/0190970 A1 | 7/2015 | Itagaki | |
| 2015/0238148 A1 | 8/2015 | Georgescu et al. | |
| 2015/0343708 A1 | 12/2015 | Gerstle et al. | |
| 2015/0347709 A1 | 12/2015 | Mansi et al. | |
| 2016/0129637 A1* | 5/2016 | Zhou | B33Y 50/00 700/98 |
| 2016/0166220 A1* | 6/2016 | Bar-Shalev | A61B 6/4417 600/427 |
| 2016/0174902 A1 | 6/2016 | Georgescu et al. | |
| 2017/0057169 A1* | 3/2017 | Grbic | B29C 64/386 |

OTHER PUBLICATIONS

Yang et al., "Prediction Based Collaborative Trackers (PCT): A Robust and Accurate Approach Toward 3D Medical Object Tracking", IEEE Transactions on Medical Imaging, 2011, vol. 30, No. 11, pp. 1921-1932.

Mansi et al., "Virtual Pulmonary Valve Replacement Interventions with a Personalized Cardiac Electromechanical Model", In Recent Advances in the 3D Physiological Hume, 2009, Springer London, pp. 75-90.

Kayvanpour et al., "Towards Personalized Cardiology: Multi-Scale Modeling of the Failing Heart", PloS One, (10)7: e0134369.doi:10.1371/journal.pone.0134869, 2015.

* cited by examiner

MULTI-MODALITY IMAGE FUSION FOR 3D PRINTING OF ORGAN MORPHOLOGY AND PHYSIOLOGY

This application claims the benefit of U.S. Provisional Application No. 62/288,481, filed Jan. 29, 2016, the disclosure of which is herein incorporated by reference in its entirety.

BACKGROUND OF THE INVENTION

The present invention relates to 3D printing of an organ based on medical image data, and more particularly to multi-modality image fusion for 3D printing of organ morphology and physiology from multiple imaging modalities.

3D printing has seen tremendous progress in recent years. Recent advances in material design. Current medical applications rely on simple anatomical modeling based on a single medical imaging modality, most commonly computed tomography (CT). 3D printing can be performed locally, via 3D printers such as MakerBot or more advanced devices, or via services (e.g., Materialise or ShapeWays). However, the printed models come from a single medical imaging modality and only limited printing capabilities are available.

BRIEF SUMMARY OF THE INVENTION

The present invention provides a method and system for multi-modality image fusion for 3D printing of organ morphology and physiology. Different image modalities provide different information on an organ. It is therefore desirable to go beyond the current mono-modality status quo and provide a tool that enables fusing of information from multiple medical imaging modalities into a single model and printing such a fused model using 3D printing. The present inventors have recognized that generating a 3D printed model that combines morphological, structural, dynamic, and functional information from various medical imaging modalities would be a great use in the clinical workflow, facilitating decision making, therapy planning, discussions during clinical board meetings, teaching to patients, and device development. Embodiments of the present invention utilize a framework that relies on image analytics, semantic image fusion, and advanced materials for 3D printing of organ models. Embodiments of the present invention combine the information from multiple imaging sources to create a holistic model of an organ, including morphology, substrate, and physiology, and prints the holistic model using 3D printing with advanced materials.

In one embodiment of the present invention, a plurality of medical images of a target organ of a patient from different medical imaging modalities are fused. A holistic mesh model of the target organ is generated by segmenting the target organ in the fused medical images from the different medical imaging modalities. One or more spatially varying physiological parameter is estimated from the fused medical images and the estimated one or more spatially varying physiological parameter is mapped to the holistic mesh model of the target organ. The holistic mesh model of the target organ is 3D printed including a representation of the estimated one or more spatially varying physiological parameter mapped to the holistic mesh model.

These and other advantages of the invention will be apparent to those of ordinary skill in the art by reference to the following detailed description and the accompanying drawings.

DETAILED DESCRIPTION

The present invention relates to multi-modality image fusion for 3D printing of organ morphology and physiology. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or available through a network system.

Different image modalities provide different information on an organ. In cardiology for instance, ultrasound is typically the modality of choice for cardiac function, computed tomography (CT) for cardiac morphology, and magnetic resonance (MR) for tissue substrate. Similarly for the liver, ultrasound can provide flow and elasticity, CT can provide anatomy, and MR can provide tissue substrate (fibrosis, fat, etc.). Embodiments of the present invention go beyond the current mono-modality status quo and provide a tool that enables fusing of information from multiple medical imaging modalities into a single model and printing such a fused model using recent advances in 3D printing, such as advances in material design that have enabled 3D-printing of dynamic shapes, colors, textures, and programmable material of all sorts. Embodiments of the present invention realize a 3D printed model that combines morphological, structural, dynamic, and functional information from various medical imaging modalities. Such a 3D printed model has many uses including in the clinical workflow, facilitating decision making, therapy planning, discussions during clinical board meetings, teaching to patients, and device development.

Figure 1:
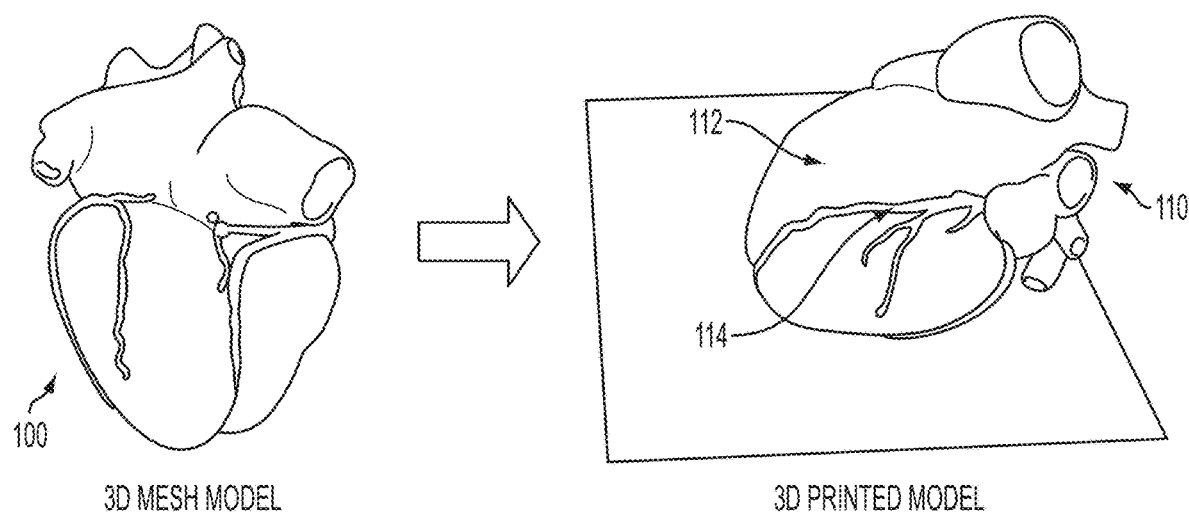
FIG. 1 illustrates and example of 3D printing an organ model from an embodiment of the present invention.

Embodiments of the present invention utilize a framework that relies on image analytics, semantic image fusion, and advanced materials for 3D printing of organ models. Embodiments of the present invention combine the information from multiple imaging sources to create a holistic model of an organ, including morphology, substrate, and physiology, and prints the holistic model using 3D printing with advanced materials. In an advantageous embodiment of the present invention, different images from multiple imaging modalities are fused into a single coordinate system using robust, semantic image registration and data fusion. Components of interest of then segmented on the best available modality (e.g., morphology from CT, tissue substrate like fibrosis, scar, and tumors from MR) and fused to build a holistic 3D mesh model of the organ of interest. If a same "organ part" can be estimated or segmented from two or more modalities, a consensus can be derived (e.g., average mesh, voting, etc.). Tissue substrate and properties are estimated through direct imaging measurement (e.g., strain, scar, fibrosis, elasticity from ultrasound, MR, electrography), or indirectly using computational physiological models (e.g., electrical conductivity, stiffness, stress), and this information is mapped to the holistic model as spatially varying, potentially dynamic mesh data. The holistic model is then 3D-printed. Mesh data can be represented though color coding (static or dynamic), spatially varying material texturing, and/or even dynamic shape morphing (through shape memory for instance. FIG. 1 illustrates and example of 3D printing an organ model from an embodiment of the present invention. As illustrated in FIG. 1, a 3D mesh model 100 that is a fusion of CT-based cardiac chambers and coronary arteries is generated and a 3D printed model 110 is created from the 3D mesh model 100. The resulting 3D printed model 110 in FIG. 1 is printed with different color materials representing the muscle 112 and the coronary arteries 114.

Figure 2:
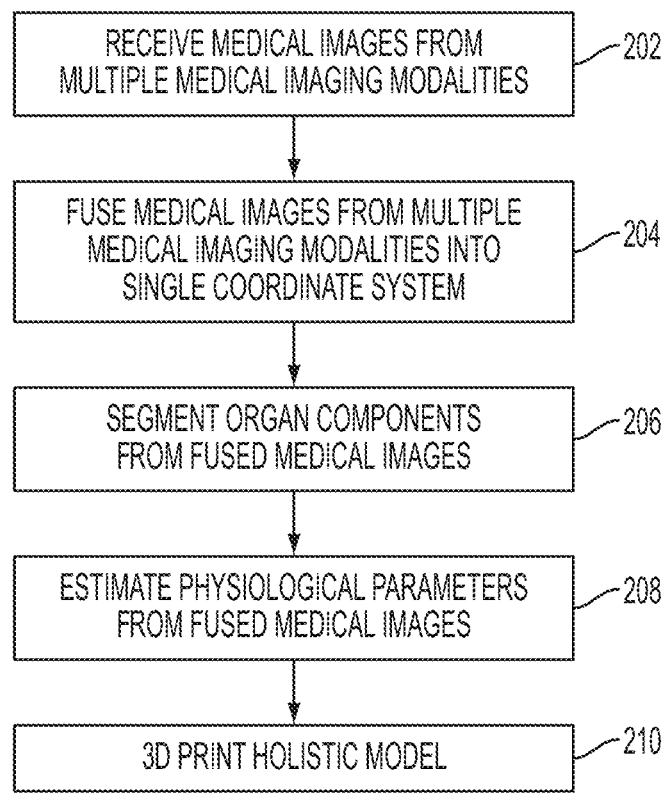
FIG. 2 illustrates a method for multi-modality image fusion for 3D printing of a holistic patient-specific organ model according to an embodiment of the present invention.

FIG. 2 illustrates a method for multi-modality image fusion for 3D printing of a holistic patient-specific organ model according to an embodiment of the present invention. The method of FIG. 2 generates a 3D printed model of a target organ (or other anatomical structure) that includes information fused from multiple medical imaging modalities, such as morphology, substrate, and physiology information. Although the method of FIG. 2 describes generating a 3D printed model for a target organ, the method is not limited only to organs, and can be similarly applied to generate a patient-specific 3D printed model for any anatomical structure or a 3D printed model including multiple organs or anatomical structures.

Referring to FIG. 2, at step 202, medical images from multiple medical imaging modalities are received. The medical images can include a medical images of the target organ acquired using a plurality of medical imaging modalities. For example, medical images from a plurality of medical imaging modalities, such as CT, MR, ultrasound, positron emission tomography (PET), Dyna-CT, x-ray, etc., can be received. In an advantageous embodiment, the medical images received from the various medical imaging modalities are 3D medical images and/or 4D (3D+t) medical image data (i.e., a time-sequence of 3D medical images). However, 2D medical images for one or more modalities may also be received. The medical images from one or more of the medical imaging modalities may be received directly from image acquisition devices used to acquire the medical images, such as a CT scanner, MR scanner, ultrasound image acquisition device, etc. Alternatively, the medical images from one or more of the medical imaging modalities may be received by loading previously acquired medical images from a storage or memory of a computer device, a portable computer readable medium, or a remote database, or by receiving the medical images via electronic transmission from a remote computer device.

At step 204, the medical images from the multiple medical imaging modalities are fused into a single coordinate system. Semantic image registration can be used to combine/fuse the medical image information from the different imaging modalities. In a possible implementation, standard rigid and/or non-rigid image registration techniques can be used to register the medical images from the different imaging modalities. However, advantageous embodiments of the present invention utilize machine-learning for more robust image fusion. In advantageous implementations, the machine-learning based registration focuses on the organ of interest (target organ) as seen in both images to perform the registrations, while disregarding other image features that can be misleading. Such a semantic approach therefore increases robustness of the fusion while simultaneously improving the accuracy.

Figure 3:
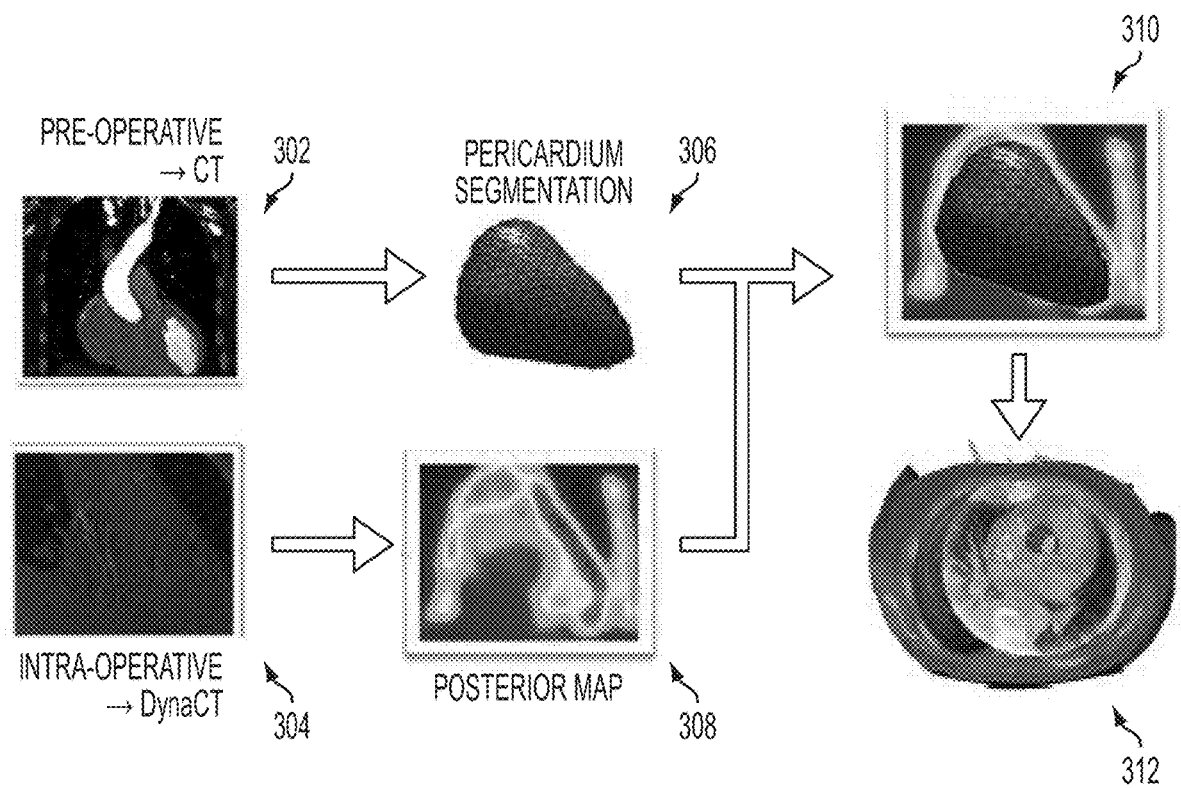
FIG. 3 illustrates an example semantic registration of CT and DynaCT images using cardiac pericardium information.
Figure 4:
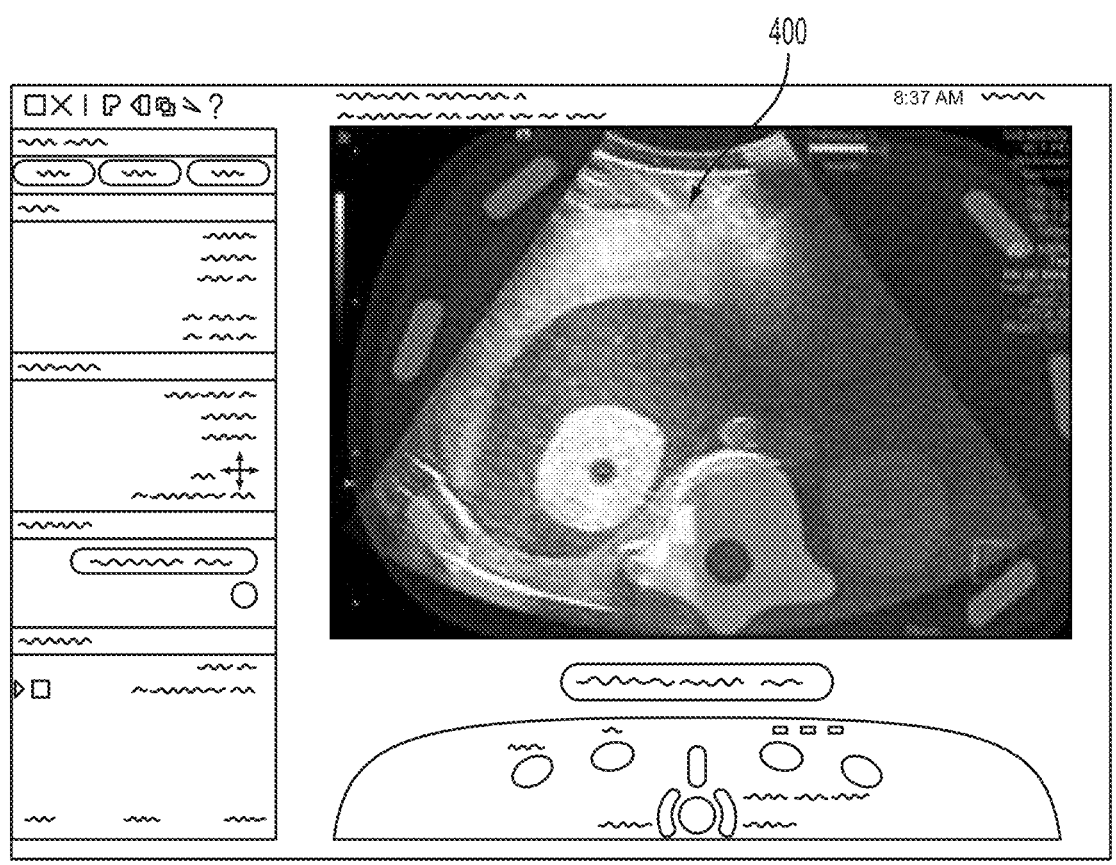
FIG. 4 illustrates an example of a fused image resulting from registering CT and ultrasound images.

In one embodiment, in order to fuse the medical images from the multiple medical imaging modalities, machine-learning is used to estimate semantic/organ-specific features that are then used as a similarity metric. In this embodiment, the registration focuses only on the organ of interest, thus increasing the overall robustness. For example, the registration can be based on voxels inside the organ in the medical images, mesh points of organ meshes extracted from the medical images, or specific anatomical landmarks associated with the target organ. In a possible implementation, the registration may focus on an anchor anatomical structure instead of the target organ. An anchor anatomical structure is a structure located near the target organ that has better correspondences in the imaging modalities being registered than the target organ. In an exemplary embodiment, in order to register two medical images from different imaging modalities, the organ of interest or specific components of the organ of interest can be segmented in each of the images and an optimal transformation can be calculated using the points of the segmented organ of interest. In another exemplary embodiment, the organ if interest can be segmented in one image and a probability map for the organ of interest can be extracted from the other image by applying a trained discriminative classifier on each voxel. The registration can be then be calculated using the segmented organ of interest and the probability map using a sparse matching method, as described in Neumann et al., "Probabilistic Sparse Matching for Robust 3D/3D Fusion in Minimally Invasive Surgery", *IEEE Transactions on Medical Imaging*, Vol. 34, No. 1, pp. 49-60, 2015, which is incorporated herein by reference in its entirety. FIG. 3 illustrates an example semantic registration of CT and DynaCT images using cardiac pericardium information. As shown in FIG. 3, image 302 is a CT image and image 304 is a DynaCT image 304. Pericardium segmentation is performed in the CT image 302, resulting in a segmented pericardium mesh 306. A posterior probability map 308 is extracted from the DynaCT image 304 using a trained discriminative classifier. A transformation is then found to optimally align the segmented pericardium mesh 306 to the posterior probability map 308. Image 310 shows the segmented pericardium mesh 306 aligned to the posterior probability map 308. The transformation is then used to register or fuse the CT image 302 to the DynaCT image 304. Image 312 shows a 3D view of a CT image fused with a DynaCT image. FIG. 4 illustrates an example of a fused image 400 resulting from registering CT and ultrasound images.

In another embodiment, an artificial agent is trained to efficiently perform the registration task itself using deep reinforcement learning. A neural network is trained, where the two images are given as input, and the output is a Q-value for each possible task the artificial agent can perform (e.g., move image up, down, etc.) Based on the current state of the input images, the trained neural network calculates a Q-value for each possible action/task. The tasks correspond to possible actions that can be applied to adjust one image to match the other image, including moving the image in various directions and adjusting the orientation and scale of an image. The task with the highest Q-value is selected and applied to the images. The trained neural network is then used to calculate the Q-value for each possible task based on the updated state of the images, and the task with the highest Q-value is again selected and applied to the images. This procedure can be repeated for a predetermined number of iterations or until convergence. By parameterizing the action space (i.e., the deformation field model), any registration task can potentially be learned using this method.

In another embodiment, the space of deformations is learned from a set of training examples using manifold learning (linear or non-linear). The registration algorithm then operates within that space through direct constraints of projection techniques.

Returning to FIG. 2, at step 206, organ components are segmented from the fused medical images. Using each of the available images, a holistic 3D (or 3D+time) mesh model of the organ to print is estimated using robust image analytics and machine learning. Organ components are segmented on the best available imaging modality, and fused using masks and/or mesh operations. For a particular target organ (e.g., heart, liver, etc.), the best imaging modality or modalities for various organ components of the target organ can be pre-specified. For example, information that specifies one or more best imaging modality for each organ component can be stored and used to determine which imaging modality to use to segment each organ component. Because all of the images from the different medical imaging modalities are co-registered in step 204, mesh creation and composition for the target organ can be performed seamlessly using organ components segmented in different medical images. In a case in which the same structure (e.g., organ or organ component) can be reliably segmented in more than one of the available imaging modalities, a mesh fusion approach based on spatially-varying "confidence" weighting can be used to combine segmentation results for the same structure from different imaging modalities. For example, the boundary points of the segmented structure in each of the imaging modalities can be weighted according to the intensity gradient at the model boundary and then combined using a weighted average. A shape model is then employed to regularize the result. The types of medical imaging modalities used for various organ components may vary depending on the target organ. For example, for the heart or the liver, CT, ultrasound, and/or MR can be used to provide cardiac anatomy and morphology, and MR can be used to provide tissue substrate.

Traditional and/or machine-learning based techniques can be employed for the segmentation tasks. For example, segmentation can be performed using a level-set optimization method, such as the method described in U.S. Pat. No. 9,042,620, issued May 26, 2015, and entitled "Method and System for Multi-Organ Segmentation Using Learning-Based Segmentation and Level-Set Optimization", which is incorporated herein by reference in its entirety, or by using a Marginal Space Learning (MSL) based segmentation method, such as the method described in U.S. Pat. No. 7,916,919, issued Mar. 29, 2011, and entitled "System and Method for Segmenting Chambers of a Heart in a Three Dimensional Image", which is incorporated herein by reference in its entirety. The idea of MSL is not to learn a monolithic classifier directly in the full parameter space of similarity transformations but to incrementally learn classifiers on marginal parameter spaces. In particular, the detection of a 3D anatomical object (e.g., organ or organ component) can be split into three problems: position estimation, position-orientation estimation, and position-orientation-scale estimation. A separate classifier is trained based on annotated training data for each of these estimation problems. The classifiers in the lower dimensional marginal spaces are used to prune the searching space efficiently. This object localization stage results in an estimated transformation (position, orientation, and scale) of the object. After automatic object localization, a mean shape model of the object is aligned with the estimated transformation to get a rough estimate of the object shape. The shape is then deformed locally to fit the object boundary using an active shape model (ASM) and a machine learning based boundary detector. Additional details regarding MSL-based segmentation are described in U.S. Pat. No. 7,916,919 and United States Published Patent Application No. 2012/0022843, which are incorporated herein by reference in their entirety. Deep Learning based object detection methods may also be used to perform the segmentation of the target organ and/or target organ components. For example, Marginal Space Deep Learning (MSDL) or Marginal Space Deep Regression (MSDR) can be used to perform the 3D object segmentation, as described in United States Published Patent Application No. 2015/0238148 and United States Published Patent Application No. 2016/0174902, which are incorporated herein by reference in their entirety. Relying on shape models, the above segmentation approaches provide consistent mesh parameterization (i.e., point correspondence) across medical imaging modalities, patients and time, thus enabling seamless and robust mesh fusion and other operations.

Figure 5:
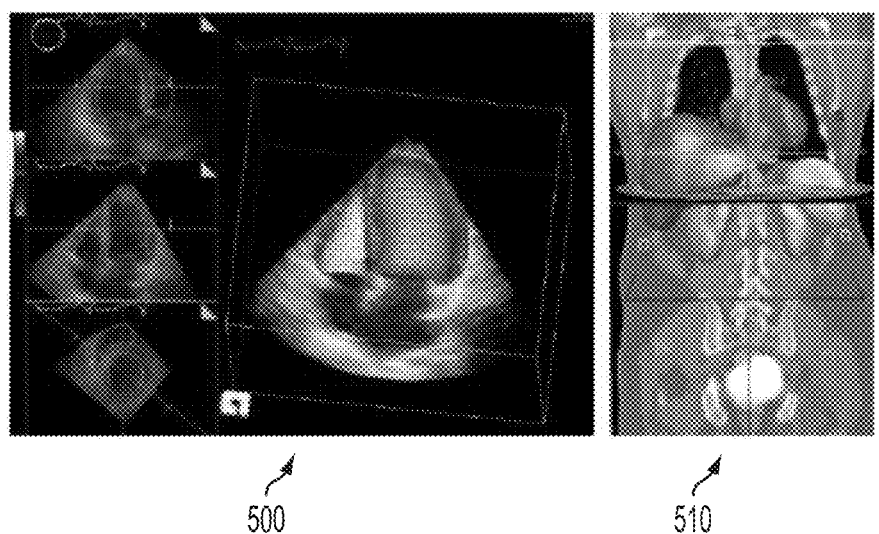
FIG. 5 illustrates exemplary segmentation results in different medical imaging modalities.

FIG. 5 illustrates exemplary segmentation results in different medical imaging modalities. As shown in FIG. 5, image 500 shows an example of heart chamber segmentation in an ultrasound image. Image 510 shows an example of multi-organ segmentation in a CT image. It is to be understood that the learning-based segmentation methods used to generate the segmentation results shown in FIG. 5 can be similarly applied to other imaging modalities as well.

Figure 6:
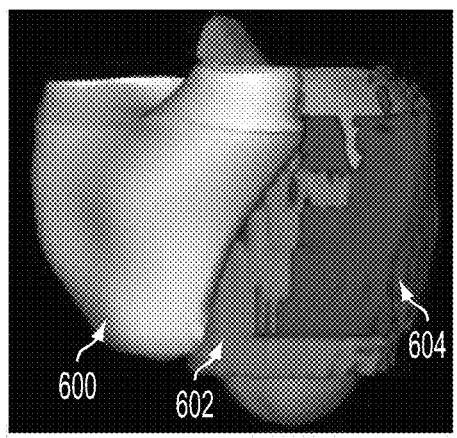
FIG. 6 illustrates an example of mapping segmented abnormal tissue information to a mesh model of a target organ.

In addition to segmenting organ boundaries, the image segmentation techniques described above can be similarly applied to efficiently segment different/abnormal tissue types, such as scar tissue, border zone (healing) tissue, fibrosis, tumors, and/or fat tissue in the target organ. That is portions of the target organ/anatomical structure for which the tissue substrate is different from the standard healthy tissue (e.g., muscle) are segmented in the medical images. According to an advantageous implementation, the tissue substrate information for the target organ (e.g., heart, liver, etc.) can be segmented from MR images. The segmented abnormal tissue (e.g., scar, fibrosis, tumor, fat, etc.) is then mapped to the mesh model of the target organ. FIG. 6 illustrates an example of mapping segmented abnormal tissue information to a mesh model of a target organ. As shown in FIG. 6, a cardiac model 600 of the heart chambers is estimated from cine MRI. Scar tissue 602 and healing tissue 604 is segmented from delayed enhanced magnetic resonance imaging (DE-MRI) and mapped to the cardiac model 600. Once the anatomy/morphology of the target organ and/or organ components is/are segmented and the segmented tissue substrate information is mapped to the organ mesh, a holistic, unified mesh model of the target organ is created.

Returning to FIG. 2, at step 208, physiological parameters are estimated from the fused medical images and added to the holistic mesh model of the target organ. Various tissue properties, tissue dynamics, and tissue activity can be estimated through direct measurement from the medical images (e.g., ultrasound, MR, elastography), or indirectly using computational physiological models, and this physiological information is mapped to the holistic model as spatially varying, potentially dynamic mesh data. The physiological and dynamic parameters can be mapped to each point in the holistic mesh model, such that a respective vector of values for various physiological and dynamic parameters is stored for each point in the holistic mesh model. Some of the physiological and dynamic parameters may vary with time as well, such that values for these parameters for a predetermined number of time steps may be stored for each point in the holistic mesh model.

Tissue dynamics can be estimated and mapped to the holistic mesh model. Image and feature tracking algorithms can be used to estimate a moving model of the organ of interest. For example, tracking algorithms that can track movement of a target organ are described in U.S. Pat. No. 8,577,177, issued Nov. 5, 2013 and entitled "Symmetric and Inverse-Consistent Deformable Registration", Yang et al., "Prediction Based Collaborative Trackers (PCT): A Robust and Accurate Approach Toward 3D Medical Object Tracking", *IEEE Transactions on Medical Imaging*, Vol. 30, No. 11, pp: 1921-1932, 2011, and United States Published Patent Application No. 2012/0078097, which are incorporated herein by reference in their entirety. A deformation field can then be derived from the moving model of the organ of interest. The deformation field can be a point-wise deformation field or a dense deformation field. Dynamic parameters, such as strain, velocity, etc., are then calculated from the deformation field and mapped to corresponding locations on the holistic mesh model.

Tissue properties can also be estimated and mapped to the holistic mesh model. For example, spatially varying biomechanical properties like stiffness can be mapped to the holistic mesh model. Stiffness can be measure directly using elastography techniques, such as acoustic radiation force impulse imaging (AFRI) or MR elastography. Alternatively, inverse modeling can be utilized to estimate spatially varying biomechanical parameters (e.g., stiffness) of the target organ. In particular, a biomechanical model is fitted to the patient data in the medical images and parameter identification methods are used to estimate the patient-specific parameters of the constitutive law that produces simulated movement of the target organ that best matches the observed movement of the target organ of the patient in the medical images. For example, a biomechanical model of cardiac tissue an inverse modeling can be used to estimate cardiac stiffness (Young's modulus) and active stress from observed motion of the cardiac tissue in medical images and invasive pressure measurements, as described in United States Published Patent Application No. 2013/0197881, entitled "Method and System for Patient Specific Planning of Cardiac Therapies on Preoperative Clinical Data and medical Images", U.S. Pat. No. 9,129,053, issued Sep. 8, 2015 and entitled "Method and System for Advanced Measurements Computation and Therapy Planning from Medical Data and Images Using a Multi-Physics Fluid-Solid Heart Model", and United States Published Patent Application No. 2015/0347709, entitled "Method and System for Interactive Computation of Cardiac Electromechanics", which are incorporated herein by reference in their entirety. As described in United states Published Patent Application No. 2015/0073765, entitled "System and Method for Prediction of Respiratory Motion From 3D Thoracic Images", which is incorporated herein by reference in its entirety, a biomechanical model of the lungs and inverse modeling are used to estimate a patient-specific spatially varying lung pressure field from 4D (3D+time) CT images.

Physiological tissue activity parameters can also be estimated and mapped to the holistic mesh model. For example, given electrophysiology measurements (e.g., ECG, endocardial EP mappings, body surface mapping (BSM) etc.), a medical image of the heart, and a computational model of cardiac electrophysiology, tissue electrical conductivity can be estimated non-invasively using inverse modeling to find spatially varying tissue electric conductivity values for which the simulated electrophysiology data estimated by the computational model of cardiac electrophysiology best matches the electrophysiology measurements. A method for estimating patient-specific electrical conductivity from EP measurements and medical image data using a computational heart model is described in greater detail in U.S. Pat. No. 9,463,072, issued Oct. 11, 2016 and entitled "System and Method for Patient Specific Planning and Guidance of Electrophysiology Interventions", which is incorporated herein by reference in its entirety. The electrical conductivity information can then be mapped to the holistic mesh model. Other electrophysiological parameters, such as electrical activation time, action potential duration, etc., can also be estimated using such a computational model of cardiac electrophysiology, and then mapped to the holistic mesh model. Similarly, other simulated physiological parameters such as blood flow in vessels and derived physiological parameters (e.g., pressure drop, fractional flow reserve, etc.) can be estimated using computational models and mapped to the holistic mesh model.

Figure 7:
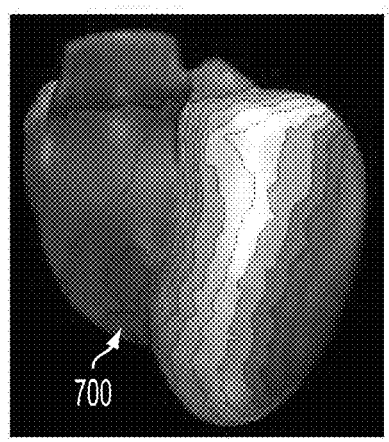
FIG. 7 illustrates an example of a color-coded cardiac electrical activation map.

In addition to storing a respective vector of values of the physiological parameters for each point in the holistic mesh model, the above described physiological information can be mapped through color coding, with a user-specific transfer function, and/or through texture coding. For example, in a possible implementation, cardiac electrical properties can be color coded, while strain maps can be associated with (and then printed with) different material texture levels. The maps can be either static or time varying. Libraries of color/texture mapping may be offered to the user to allow the user to customize how the various physiological parameters are represented on the 3D printed model. FIG. 7 illustrates an example of a color-coded cardiac electrical activation map 700. In the example of FIG. 6, cardiac electrical activation values were estimated using ultrasound data, 12-lead ECG measurements, and a computational model of cardiac electrophysiology. The electrical activation values were then mapped to the holistic mesh model of the heart, with different colors representing different ranges of electrical activation values, resulting in the color-coded cardiac electrical activation map 700. The color coding representing the different electrical activation values can then be 3D printed as different colored material or different texture material.

At step 210, the holistic model of the target organ is 3D printed. In an advantageous embodiment, the holistic model is exported as one or several stereolithography (STL) models and associated texture files, which are sent to a 3D printer, and then the 3D printer synthesizes a physical 3D model of the target organ from the holistic model. It is to be understood that the present invention is not limited to the STL file format, and the holistic model may exported using other 3D printing file formats (e.g., Additive Manufacturing File (AMF) format) as well. The 3D printer may using any type of 3D printing technology to perform, including but not limited to Stereolithography, Digital Light Processing (DCP), Fused Deposition Modeling (FDM), Selective Laser Sintering (SLS), Selective Laser Melting (SLM), Electronic Beam Melting (EBM), and Laminated Object Manufacturing (LOM).

According to an advantageous embodiment of the present invention, from the STL (or other file format) model(s) and associated text files representing the 3D holistic model, the 3D printer prints the patient-specific anatomy (shape) of the target organ defined in the 3D holistic model with materials having material properties, colors, and textures that represent various physiological and/or anatomical parameters of interest. The 3D printed model may be printed with material properties (e.g., stiffness) that vary to mimic the estimated spatially varying organ stiffness. Alternatively, the material properties (e.g., stiffness) of the material used to 3D print the model may be used to represent other parameters of interest. The user may select a parameter of interest to be represented by the material stiffness prior to the 3D printing. The 3D printed model may be printed with spatially varying material colors (static, multiple, or dynamic) to represent a particular parameter estimated from the medical images (e.g., strain, EP, conductivity, etc.). Different colors may also be used to represent different types of tissue (e.g., scar, fibrosis, fat, tumor, etc.) or to represent different anatomical structures or components of the target organ. In a possible implementation, an Organic Light Emitting Diode (OLED)-like material may be directly embedded into the 3D printed object, such that the colors on the 3D printed object can be changed in response to an electrical current. In this case, an interface can be displayed to allow a user to select the model information (parameter) to display. In response, to a user selection of a particular parameter (e.g., strain, EP, conductivity, etc.), electrical signals are sent to the OLED-like material embedded in the 3D printed model to change the color coding of the 3D printed model to represent the selected parameter. The 3D printed model may be printed may be printed with spatially varying material texture to represent a particular parameter estimated from the images (e.g., strain, EP, conductivity, etc.). Different material textures may also be used to represent different types of tissue (e.g., scar, fibrosis, fat, tumor, etc.) or to represent different anatomical structures of components of the target organ.

In a possible embodiment, material programming or similar technology can be employed to 3D print a dynamic object, for example to print a beating heart model or a moving lung model. The dynamic movement information can be obtained directly from the medical images via organ tracking over a particular time period (e.g., a cardiac cycle or a respiratory cycle).

In another possible embodiment, the holistic mesh model can be used to implement bio-printing with specific cellular properties or scaffold printing for tissue growth. The parameters can be obtained from simulations, where the user can alter the holistic model in-silico to re-establish its normal state. Simulations can be performed via mesh operations (for surgery for instance) or using a more advanced computational model of organ physiology, such as the computational models described in U.S. Pat. No. 8,920,332, issued Dec. 30, 2014 and entitled "Valve Treatment Simulation From Medical Diagnostic Imaging Data", Mansi et al., "Virtual Pulmonary Valve Replacement Interventions With a Personalised Cardiac Electromechanical Model", In *Recent Advances in the 3D Physiological Human*, pp. 75-90, Springer London, 2009, and Kayvanpour et al., "Towards Personalized Cardiology: Multi-Scale Modeling of the Failing Heart", *PloS ONE* (10)7: e0134869, 2015, which are incorporated herein by reference in their entirety.

In another possible embodiment, sensors and electrical systems can be directly printed on the 3D printed model to measure pressure, strain, temperature (passive sensing), or to stimulate the printed material (e.g., integrated pacing/ICD system). In an exemplary implementation, the electrical system can also control the shape and or a material property (e.g., stiffness) of the printed material, for remote material control and adjustment.

Figure 8:
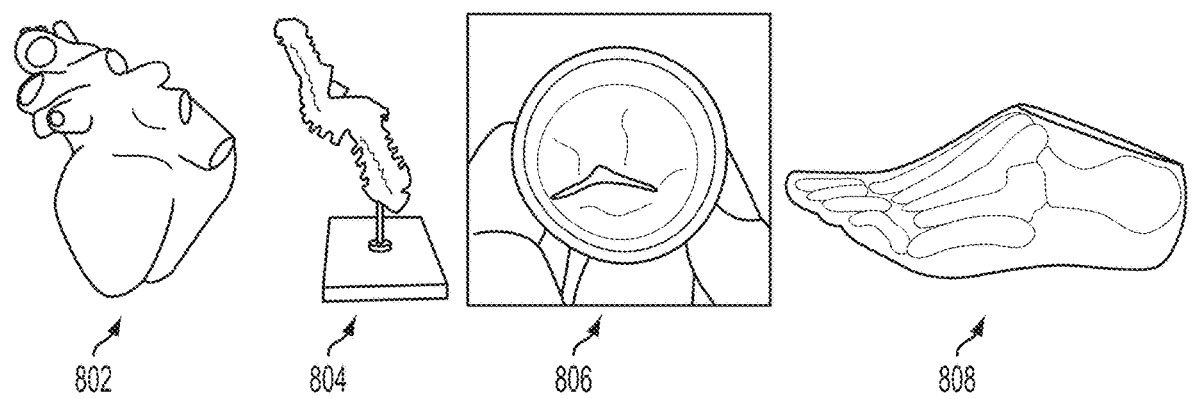
FIG. 8 illustrates exemplary patient-specific 3D printed models.

FIG. 8 illustrates exemplary patient-specific 3D printed models. Image 802 of FIG. 8 shows a patient-specific 3D printed model of a heart. Image 804 of FIG. 8 shows a patient-specific 3D printed model of a spine. Image 806 of FIG. 8 shows a patient-specific 3D printed model of an aortic valve. Image 808 of FIG. 8 shows a patient-specific 3D printed model of a foot.

Figure 9:
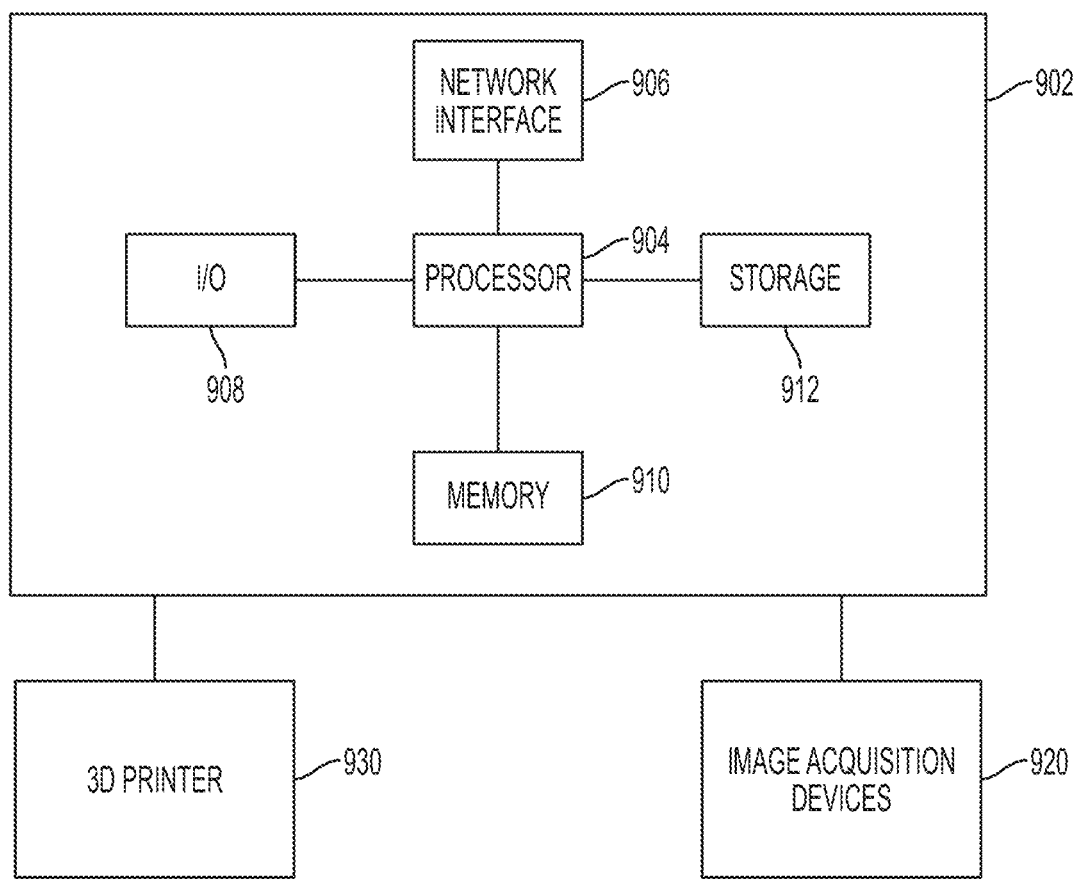
FIG. 9 is a high-level block diagram of a computer capable of implementing the present invention.

The above-described method for multi-modality image fusion for 3D printing of a holistic patient-specific organ model can be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIG. 2 may be defined by the computer program instructions stored in the memory 910 and/or storage 912 and controlled by the processor 904 executing the computer program instructions. One or more image acquisition devices 920, such as a CT scanning device, C-arm image acquisition device, MR scanning device, Ultrasound device, etc., can be connected to the computer 902 to input image data to the computer 902. It is possible that the computer and one or more of the image acquisition devices 920 may be implemented as one device. It is also possible that the image acquisition devices 920 and the computer 902 communicate wirelessly through a network or wireless communication protocol. A 3D printer 930 can be connected to the computer 902 to receive 3D model information from the computer 902 and generate a 3D printed model. The 3D printer 930 may be connected to the computer 902 via a wire or may communicate wirelessly through a network or wireless communication protocol. In a possible embodiment, the computer 902 and/or the 3D printer 930 may be located remotely with respect to the image acquisition devices 920 and may perform the method steps as part of a server or cloud based service. In another possible embodiment, the 3D printer may be located remotely with respect to the computer 902 and the 3D printing operation may be performed as part of a server or cloud based service. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate volumes received from the image acquisition device 920. One skilled in the art will recognize that an implementation of an actual computer could contain other components as well, and that FIG. 9 is a high level representation of some of the components of such a computer for illustrative purposes.

The above-described methods for multi-modality image fusion for 3D printing of a holistic patient-specific organ model may be implemented using computers operating in a client-server relationship or operating as a cloud-based service. Typically, in such a system, the client computers are located remotely from the server computer and interact via a network. The client-server relationship may be defined and controlled by computer programs running on the respective client and server computers. In this case, the method steps may be performed on any combination of the client and server computers.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for generating a patient-specific 3D printed model of a target organ from multiple medical imaging modalities, comprising:
    fusing a plurality of medical images of a target organ of a patient from different medical imaging modalities;
    generating a holistic mesh model of the target organ by segmenting the target organ in the fused medical images from the different medical imaging modalities, wherein generating a holistic mesh model of the target organ by segmenting the target organ in the fused medical images from the different medical imaging modalities comprises:
        segmenting a mesh model of the target organ from one or more of the plurality of medical images from the different medical imaging modalities,
        segmenting tissue substrate information for the target organ in a medical image in the plurality of medical images from the different medical imaging modalities other than the one or more of the plurality of medical images from which the mesh model of the target organ is segmented, and
        mapping the segmented tissue substrate information to the mesh model of the target organ, resulting in the holistic mesh model of the target organ;
    estimating one or more spatially varying physiological parameters from the fused medical images and mapping the estimated one or more spatially varying physiological parameters to the holistic mesh model of the target organ; and
    3D printing the holistic mesh model of the target organ including a representation of the estimated one or more spatially varying physiological parameters mapped to the holistic mesh model.

2. The method of claim 1, wherein fusing a plurality of medical images of a target organ of a patient from different medical imaging modalities comprises:
    estimating semantic features specific to the target organ in each of the plurality of medical images using machine learning based detection; and
    registering the plurality of medical images based on a similarity metric between the semantic features specific to the target organ in each of the plurality of medical images.

3. The method of claim 2, wherein estimating semantic features specific to the target organ in each of the plurality of medical images using machine-learning based detection comprises estimating a boundary of the target organ, and registering the plurality of medical images based on a similarity metric between the semantic features specific to the target organ in each of the plurality of medical images comprises registering the plurality of medical images based on a similarity metric between voxels within the estimated boundary of the target organ in each of the plurality of medical images.

4. The method of claim 2, wherein estimating semantic features specific to the target organ in each of the plurality of medical images using machine learning based detection comprises segmenting a mesh of the target organ in each of the plurality of medical images, and registering the plurality of medical images based on a similarity metric between the semantic features specific to the target organ in each of the plurality of medical images comprises registering the plurality of medical images based on a similarity metric between corresponding mesh points of the meshes of the target organ segmented in each of the plurality of medical images.

5. The method of claim 2, wherein estimating semantic features specific to the target organ in each of the plurality of medical images using machine learning based detection comprises segmenting a mesh of the target organ in a first one of the plurality of medical images and estimating a probability map for the target organ using a trained discriminative classifier in a second one of the plurality of medical images, and registering the plurality of medical images based on a similarity metric between the semantic features specific to the target organ estimated in each of the plurality of medical images comprises registering the first and second ones of the plurality of medical images based on a similarity metric between mesh points of the mesh of the target organ segmented in the first one of the plurality of medical images and the probability map for the target organ estimated in the second one of the plurality of medical images.

6. The method of claim 2, wherein the semantic features are anatomical landmarks associated with the target organ.

7. The method of claim 1, wherein fusing a plurality of medical images of a target organ of a patient from different medical imaging modalities comprises:
    registering a first one of the plurality of medical images and a second one of the plurality medical images using a neural network trained using deep reinforcement learning to iteratively select an action having a highest Q-value from a set of actions corresponding to adjustments to a deformation field between the first and second ones of the plurality of medical images based on a current state of the first and second ones of the plurality of medical images.

8. The method of claim 1, wherein fusing a plurality of medical images of a target organ of a patient from different medical imaging modalities comprises:
    constraining registration of the plurality of medical images to a space of deformations learned from a set of training examples using manifold learning.

9. The method of claim 1, wherein estimating one or more spatially varying physiological parameters from the fused medical images and mapping the estimated one or more spatially varying physiological parameters to the holistic mesh model of the target organ comprises:
estimating a moving model of the target organ from the fused medical images;
deriving a deformation field from the moving model of the target organ;
calculating at least one dynamic spatially varying physiological parameter from the deformation field; and
mapping the at least one dynamic spatially varying physiological parameter to the holistic mesh model.

10. The method of claim 9, wherein the at least one dynamic spatially varying physiological parameter is at least one of strain or velocity.

11. The method of claim 1, wherein estimating one or more spatially varying physiological parameters from the fused medical images and mapping the estimated one or more spatially varying physiological parameters to the holistic mesh model of the target organ comprises:
estimating a spatially varying biomechanical parameter of the target organ by fitting a biomechanical model for the target organ to one or more medical images in the plurality of medical images using inverse modeling; and
mapping the estimated spatially varying biomechanical parameter of the target organ to the holistic mesh model of the target organ.

12. The method of claim 11, wherein the biomechanical parameter is tissue stiffness.

13. The method of claim 1, wherein estimating one or more spatially varying physiological parameters from the fused medical images and mapping the estimated one or more spatially varying physiological parameters to the holistic mesh model of the target organ comprises:
estimating at least one spatially varying physiological activity parameter using a computational model for the target organ; and
mapping the estimated at least one spatially varying physiological parameter to the holistic mesh model.

14. The method of claim 13, wherein the least one spatially varying physiological activity parameter is tissue electrical conductivity, and estimating at least one spatially varying physiological activity parameter using a computational model for the target organ comprises:
estimating spatially varying tissue electrical conductivity by fitting a computational electrophysiology model of the target organ to electrophysiology measurements of the patient and at least one medical image in the plurality of medical images from different medical imaging modalities.

15. The method of claim 13, wherein the at least one spatially varying physiological activity parameter includes at least one of tissue electrical conductivity, electrical activation time, action potential duration, blood flow, or pressure drop.

16. The method of claim 1, wherein 3D printing the holistic mesh model of the target organ including a representation of the estimated one or more spatially varying physiological parameters mapped to the holistic mesh model comprises:
3D printing the holistic mesh model of the target organ with at least one of a spatially varying material property, spatially varying material colors, or spatially varying material textures representing the estimated one or more spatially varying physiological parameters mapped to the holistic mesh model.

17. The method of claim 16, wherein the one or more spatially varying physiological parameters include tissue stiffness, and 3D printing the holistic mesh model of the target organ with at least one of a spatially varying material property, spatially varying material colors, or spatially varying material textures representing the estimated one or more spatially varying physiological parameters mapped to the holistic mesh model comprises:
3D printing the holistic mesh model of the target organ with a material stiffness that varies to mimic the spatially varying tissue stiffness mapped to the holistic mesh.

18. The method of claim 16, wherein 3D printing the holistic mesh model of the target organ with at least one of a spatially varying material property, spatially varying material colors, or spatially varying material textures representing the estimated one or more spatially varying physiological parameters mapped to the holistic mesh model comprises:
3D printing the holistic mesh of the target organ with spatially varying material colors representing one of the one or more spatially varying physiological parameters.

19. The method of claim 16, wherein 3D printing the holistic mesh model of the target organ with at least one of a spatially varying material property, spatially varying material colors, or spatially varying material textures representing the estimated one or more spatially varying physiological parameters mapped to the holistic mesh model comprises:
3D printing the holistic mesh of the target organ with spatially varying material textures representing one of the one or more spatially varying physiological parameters.

20. The method of claim 16, wherein the one or more spatially varying physiological parameters mapped to the holistic mesh model include at least first, second, and third spatially varying physiological parameters mapped to the holistic mesh model, and 3D printing the holistic mesh model of the target organ with at least one of a spatially varying material property, spatially varying material colors, or spatially varying material textures representing the estimated one or more spatially varying physiological parameters mapped to the holistic mesh model comprises:
3D printing the holistic mesh of the target organ with a spatially varying material property representing the first spatially varying physiological parameter mapped to the holistic mesh model, with spatially varying material colors representing the second spatially varying physiological parameter mapped to the holistic mesh model, and with spatially varying material textures representing the third spatially varying physiological parameter mapped to the holistic mesh model.

21. A method for generating a patient-specific 3D printed model of a target organ from multiple medical imaging modalities, comprising:
fusing a plurality of medical images of a target organ of a patient from different medical imaging modalities;
generating a holistic mesh model of the target organ by segmenting the target organ in the fused medical images from the different medical imaging modalities;
estimating one or more spatially varying physiological parameters from the fused medical images and mapping the estimated one or more spatially varying physiological parameters to the holistic mesh model of the target organ, wherein estimating one or more spatially varying physiological parameters from the fused medical images and mapping the estimated one or more spatially varying physiological parameters to the holistic mesh model of the target organ comprises:

measuring stiffness at various points on the target organ in ultrasound elastography or magnetic resonance elastography images in the plurality of medical images from different medical imaging modalities, and mapping the stiffness measurements to the holistic mesh model; and 3D printing the holistic mesh model of the target organ including a representation of the estimated one or more spatially varying physiological parameters mapped to the holistic mesh model.

22. The method of claim 21, wherein generating a holistic mesh model of the target organ by segmenting the target organ in the fused medical images from the different medical imaging modalities comprises:

for each of a plurality of organ components of the target organ, segmenting that organ component in a medical image from a best available medical imaging modality for that organ component in the plurality of medical images; and fusing the segmentation results for the plurality of organ components to generate the holistic mesh model of the target organ.

23. The method of claim 22, wherein segmenting that organ component in a medical image from a best available medical imaging modality for that organ component in the plurality of medical images comprises:

if there are two or more best available medical imaging modalities for that organ component in the plurality of medical images, segmenting that organ component in a respective medical image from each of best available medical imaging modalities in the plurality of medical images; and fusing the segmentation results based on spatially varying confidence weighting of the segmented organ component in each of respective medical images based on a strength of an intensity gradient at a boundary of the segmented organ component in each of the respective medical image.

24. An apparatus for generating a patient-specific 3D printed model of a target organ from multiple medical imaging modalities, comprising:

means for fusing a plurality of medical images of a target organ of a patient from different medical imaging modalities;

means for generating a holistic mesh model of the target organ by segmenting the target organ in the fused medical images from the different medical imaging modalities, wherein the means for generating a holistic mesh model of the target organ by segmenting the target organ in the fused medical images from the different medical imaging modalities comprises:

means for segmenting a mesh model of the target organ from one or more of the plurality of medical images from the different medical imaging modalities, means for segmenting tissue substrate information for the target organ in a medical image in the plurality of medical images from the different medical imaging modalities other than the one or more of the plurality of medical images from which the mesh model of the target organ is segmented, and means for mapping the segmented tissue substrate information to the mesh model of the target organ, resulting in the holistic mesh model of the target organ;

means for estimating one or more spatially varying physiological parameters from the fused medical images and mapping the estimated one or more spatially varying physiological parameters to the holistic mesh model of the target organ; and means for 3D printing the holistic mesh model of the target organ including a representation of the estimated one or more spatially varying physiological parameters mapped to the holistic mesh model.

25. The apparatus of claim 24, wherein the means for fusing a plurality of medical images of a target organ of a patient from different medical imaging modalities comprises:

means for estimating semantic features specific to the target organ in each of the plurality of medical images using machine learning based detection; and means for registering the plurality of medical images based on a similarity metric between the semantic features specific to the target organ in each of the plurality of medical images.

26. The apparatus of claim 24, wherein the means for fusing a plurality of medical images of a target organ of a patient from different medical imaging modalities comprises:

means for registering a first one of the plurality of medical images and a second one of the plurality medical images using a neural network trained using deep reinforcement learning to iteratively select an action having a highest Q-value from a set of actions corresponding to adjustments to a deformation field between the first and second ones of the plurality of medical images based on a current state of the first and second ones of the plurality of medical images.

27. The apparatus of claim 24, wherein the means for estimating one or more spatially varying physiological parameters from the fused medical images and mapping the estimated one or more spatially varying physiological parameters to the holistic mesh model of the target organ comprises:

means for estimating a moving model of the target organ from the fused medical images;

means for deriving a deformation field from the moving model of the target organ;

means for calculating at least one dynamic spatially varying physiological parameter from the deformation field; and means for mapping the at least one dynamic spatially varying physiological parameter to the holistic mesh model.

28. The apparatus of claim 24, wherein the means for estimating one or more spatially varying physiological parameters from the fused medical images and mapping the estimated one or more spatially varying physiological parameters to the holistic mesh model of the target organ comprises:

means for estimating a spatially varying biomechanical parameter of the target organ by fitting a biomechanical model for the target organ to one or more medical images in the plurality of medical images using inverse modeling; and means for mapping the estimated spatially varying biomechanical parameter of the target organ to the holistic mesh model of the target organ.

29. The apparatus of claim 24, wherein the means for estimating one or more spatially varying physiological parameters from the fused medical images and mapping the estimated one or more spatially varying physiological parameters to the holistic mesh model of the target organ comprises:

means for estimating at least one spatially varying physiological activity parameter using a computational model for the target organ; and means for mapping the estimated at least one spatially varying physiological parameter to the holistic mesh model.

30. The apparatus of claim 24, wherein the means for 3D printing the holistic mesh model of the target organ including a representation of the estimated one or more spatially varying physiological parameters mapped to the holistic mesh model comprises:

means for 3D printing the holistic mesh model of the target organ with at least one of a spatially varying material property, spatially varying material colors, or spatially varying material textures representing the estimated one or more spatially varying physiological parameters mapped to the holistic mesh model.

31. The apparatus of claim 30, wherein the one or more spatially varying physiological parameters mapped to the holistic mesh model include at least first, second, and third spatially varying physiological parameters mapped to the holistic mesh model, and the means for 3D printing the holistic mesh model of the target organ with at least one of a spatially varying material property, spatially varying material colors, or spatially varying material textures representing the estimated one or more spatially varying physiological parameters mapped to the holistic mesh model comprises:

means for 3D printing the holistic mesh of the target organ with a spatially varying material property representing the first spatially varying physiological parameter mapped to the holistic mesh model, with spatially varying material colors representing the second spatially varying physiological parameter mapped to the holistic mesh model, and with spatially varying material textures representing the third spatially varying physiological parameter mapped to the holistic mesh model.

32. An apparatus for generating a patient-specific 3D printed model of a target organ from multiple medical imaging modalities, comprising:

means for fusing a plurality of medical images of a target organ of a patient from different medical imaging modalities;

means for generating a holistic mesh model of the target organ by segmenting the target organ in the fused medical images from the different medical imaging modalities;

means for estimating one or more spatially varying physiological parameters from the fused medical images and mapping the estimated one or more spatially varying physiological parameters to the holistic mesh model of the target organ, wherein the means for estimating one or more spatially varying physiological parameters from the fused medical images and mapping the estimated one or more spatially varying physiological parameters to the holistic mesh model of the target organ comprises:

means for measuring stiffness at various points on the target organ in ultrasound elastography or magnetic resonance elastography images in the plurality of medical images from different medical imaging modalities, and means for mapping the stiffness measurements to the holistic mesh model; and means for 3D printing the holistic mesh model of the target organ including a representation of the estimated one or more spatially varying physiological parameters mapped to the holistic mesh model.

33. The apparatus of claim 32, wherein the means for generating a holistic mesh model of the target organ by segmenting the target organ in the fused medical images from the different medical imaging modalities comprises:

means for segmenting each organ component of a plurality of organ components in a medical image from a best available medical imaging modality for that organ component in the plurality of medical images; and means for fusing the segmentation results for the plurality of organ components to generate the holistic mesh model of the target organ.

34. A non-transitory computer readable medium storing computer program instructions for generating a patient-specific 3D printed model of a target organ from multiple medical imaging modalities, the computer program instructions when executed by a processor cause the processor to perform operations comprising:

fusing a plurality of medical images of a target organ of a patient from different medical imaging modalities;

generating a holistic mesh model of the target organ by segmenting the target organ in the fused medical images from the different medical imaging modalities, wherein generating a holistic mesh model of the target organ by segmenting the target organ in the fused medical images from the different medical imaging modalities comprises:

segmenting a mesh model of the target organ from one or more of the plurality of medical images from the different medical imaging modalities, segmenting tissue substrate information for the target organ in a medical image in the plurality of medical images from the different medical imaging modalities other than the one or more of the plurality of medical images from which the mesh model of the target organ is segmented, and mapping the segmented tissue substrate information to the mesh model of the target organ, resulting in the holistic mesh model of the target organ;

estimating one or more spatially varying physiological parameters from the fused medical images and mapping the estimated one or more spatially varying physiological parameters to the holistic mesh model of the target organ; and 3D printing the holistic mesh model of the target organ including a representation of the estimated one or more spatially varying physiological parameters mapped to the holistic mesh model.

35. The non-transitory computer readable medium of claim 34, wherein fusing a plurality of medical images of a target organ of a patient from different medical imaging modalities comprises:

estimating semantic features specific to the target organ in each of the plurality of medical images using machine learning based detection; and registering the plurality of medical images based on a similarity metric between the semantic features specific to the target organ in each of the plurality of medical images.

36. The non-transitory computer readable medium of claim 34, wherein fusing a plurality of medical images of a target organ of a patient from different medical imaging modalities comprises:

registering a first one of the plurality of medical images and a second one of the plurality medical images using a neural network trained using deep reinforcement learning to iteratively select an action having a highest Q-value from a set of actions corresponding to adjustments to a deformation field between the first and second ones of the plurality of medical images based on a current state of the first and second ones of the plurality of medical images.

37. The non-transitory computer readable medium of claim 34, wherein estimating one or more spatially varying physiological parameters from the fused medical images and mapping the estimated one or more spatially varying physiological parameters to the holistic mesh model of the target organ comprises:
   estimating a moving model of the target organ from the fused medical images;
   deriving a deformation field from the moving model of the target organ;
   calculating at least one dynamic spatially varying physiological parameter from the deformation field; and
   mapping the at least one dynamic spatially varying physiological parameter to the holistic mesh model.

38. The non-transitory computer readable medium of claim 34, wherein estimating one or more spatially varying physiological parameters from the fused medical images and mapping the estimated one or more spatially varying physiological parameters to the holistic mesh model of the target organ comprises:
   estimating a spatially varying biomechanical parameter of the target organ by fitting a biomechanical model for the target organ to one or more medical images in the plurality of medical images using inverse modeling; and
   mapping the estimated spatially varying biomechanical parameter of the target organ to the holistic mesh model of the target organ.

39. The non-transitory computer readable medium of claim 38, wherein estimating one or more spatially varying physiological parameters from the fused medical images and mapping the estimated one or more spatially varying physiological parameters to the holistic mesh model of the target organ comprises:
   estimating at least one spatially varying physiological activity parameter using a computational model for the target organ; and
   mapping the estimated at least one spatially varying physiological parameter to the holistic mesh model.

40. The non-transitory computer readable medium of claim 34, wherein 3D printing the holistic mesh model of the target organ including a representation of the estimated one or more spatially varying physiological parameters mapped to the holistic mesh model comprises:
   3D printing the holistic mesh model of the target organ with at least one of a spatially varying material property, spatially varying material colors, or spatially varying material textures representing the estimated one or more spatially varying physiological parameters mapped to the holistic mesh model.

41. The non-transitory computer readable medium of claim 40, wherein the one or more spatially varying physiological parameters include tissue stiffness, and 3D printing the holistic mesh model of the target organ with at least one of a spatially varying material property, spatially varying material colors, or spatially varying material textures representing the estimated one or more spatially varying physiological parameters mapped to the holistic mesh model comprises:
   3D printing the holistic mesh model of the target organ with a material stiffness that varies to mimic the spatially varying tissue stiffness mapped to the holistic mesh.

42. The non-transitory computer readable medium of claim 40, wherein the one or more spatially varying physiological parameters mapped to the holistic mesh model include at least first, second, and third spatially varying physiological parameters mapped to the holistic mesh model, and 3D printing the holistic mesh model of the target organ with at least one of a spatially varying material property, spatially varying material colors, or spatially varying material textures representing the estimated one or more spatially varying physiological parameters mapped to the holistic mesh model comprises:
   3D printing the holistic mesh of the target organ with a spatially varying material property representing the first spatially varying physiological parameter mapped to the holistic mesh model, with spatially varying material colors representing the second spatially varying physiological parameter mapped to the holistic mesh model, and with spatially varying material textures representing the third spatially varying physiological parameter mapped to the holistic mesh model.

43. A non-transitory computer readable medium storing computer program instructions for generating a patient-specific 3D printed model of a target organ from multiple medical imaging modalities, the computer program instructions when executed by a processor cause the processor to perform operations comprising:
   fusing a plurality of medical images of a target organ of a patient from different medical imaging modalities;
   generating a holistic mesh model of the target organ by segmenting the target organ in the fused medical images from the different medical imaging modalities;
   estimating one or more spatially varying physiological parameters from the fused medical images and mapping the estimated one or more spatially varying physiological parameters to the holistic mesh model of the target organ, wherein estimating one or more spatially varying physiological parameters from the fused medical images and mapping the estimated one or more spatially varying physiological parameters to the holistic mesh model of the target organ comprises:
      measuring stiffness at various points on the target organ in ultrasound elastography or magnetic resonance elastography images in the plurality of medical images from different medical imaging modalities, and
      mapping the stiffness measurements to the holistic mesh model; and
   3D printing the holistic mesh model of the target organ including a representation of the estimated one or more spatially varying physiological parameters mapped to the holistic mesh model.

44. The non-transitory computer readable medium of claim 43, wherein generating a holistic mesh model of the target organ by segmenting the target organ in the fused medical images from the different medical imaging modalities comprises:
   for each of a plurality of organ components of the target organ, segmenting that organ component in a medical image from a best available medical imaging modality for that organ component in the plurality of medical images; and fusing the segmentation results for the plurality of organ components to generate the holistic mesh model of the target organ.

* * * * *